United States Patent [19]
DeVries

[11] Patent Number: 5,014,694
[45] Date of Patent: May 14, 1991

[54] AMBIENT PRESSURE AIR/OXYGEN BLENDER

[75] Inventor: Douglas F. DeVries, Redland, Calif.

[73] Assignee: Bird Products Corporation, Riverside, Calif.

[21] Appl. No.: 597,054

[22] Filed: Oct. 15, 1990

[51] Int. Cl.⁵ .................... A61M 16/12; A61M 16/20
[52] U.S. Cl. ............................ 128/205.24; 128/207.16
[58] Field of Search ...................... 128/205.24, 207.16; 137/625.35

[56] References Cited

U.S. PATENT DOCUMENTS

| 3,386,458 | 6/1968 | Wasserman et al. | |
|---|---|---|---|
| 3,509,895 | 5/1970 | Henneman. | |
| 3,727,627 | 4/1973 | Bird et al. | |
| 4,297,998 | 11/1981 | Christianson | 128/204.26 |
| 4,328,823 | 5/1982 | Schreiber. | |
| 4,433,685 | 2/1984 | Giorgini et al. | 128/204.26 |
| 4,436,090 | 3/1984 | Darling | 128/204.26 |
| 4,524,804 | 6/1985 | Goedecke et al. | |
| 4,540,018 | 9/1985 | Dantigraber. | |
| 4,576,159 | 3/1986 | Hahn et al. | |
| 4,592,349 | 6/1986 | Bird | 128/204.25 |
| 4,597,387 | 7/1986 | Carnegie et al. | 128/201.27 |
| 4,606,340 | 8/1986 | Ansite | 128/205.24 |
| 4,838,257 | 6/1989 | Hatch. | |
| 4,854,574 | 8/1989 | Larson et al. | 272/99 |
| 4,898,174 | 2/1990 | Fangrow, Jr. | 128/204.24 |
| 4,966,193 | 10/1990 | De Campos | 137/625.35 |

Primary Examiner—Clifford D. Crowder
Assistant Examiner—Eric P. Raciti
Attorney, Agent, or Firm—Knobbe, Martens, Olson & Bear

[57] ABSTRACT

A gas blender for use with home ventilation equipment where pressurized oxygen is mixed with ambient air, in which a double ended poppet cooperates with two valve seats which are configured and orientated so that axial motion of the double ended poppet simultaneously opens both valves to maintain a constant flow ratio, or simultaneously closes both valves to maintain a constant flow ratio. One of the valve seats may be adjustably positioned to determine the initial flow ratio of gases through the valve seats.

40 Claims, 2 Drawing Sheets

AMBIENT PRESSURE AIR/OXYGEN BLENDER

BACKGROUND OF THE INVENTION

This invention relates to the field of respiratory care, and more particularly to the care of ventilator dependent patients who require oxygen enriched breathing gas to properly maintain ventilation.

Patients suffering from neuromuscular disease, spinal cord injuries, or various chronic respiratory diseases are often unable to breathe by themselves. Typically, these patients are intubated, which refers to the placement of a tube in the trachea to provide a sealed pneumatic conduit to the lungs. Along with the intubation, the patients are typically placed on a positive pressure ventilator. A typical ventilator system would include a blender to mix incoming air and oxygen to a desired concentration, an inspiratory flow control system to control the flow of gases to the patient's lungs, and an exhalation system to control the flow of gases from the lungs.

Ventilators for hospital use are designed to receive compressed air and oxygen from the hospital gas supply system which typically provides these gases at a pressure of about 50 psig. The gas blending and flow control systems of these ventilators are designed to work with these pressurized gas sources.

In recent years an increasing number of ventilator dependent patients are being cared for in the home. This places new design constraints on ventilator systems. Compressed air is typically not available in the home as it is in hospitals. Consequently, the ventilator blending and flow control systems for home use must be designed to operate using air at ambient pressure.

The delivery of oxygen enriched gas for ventilator dependent patients is currently implemented in one of two ways. In the first type of gas delivery system, a continuous flow of 100% oxygen from a pressurized cylinder is metered through a flow valve and meter. This flow is injected directly into the patient circuit. The proper flow rate is calculated for each ventilation condition to obtain the desired oxygen concentration from equations known in the art.

As the calculation requires knowing the minute volume and the desired oxygen concentration, this method has the disadvantage that the minute ventilation of the patient must be known. For patients who breathe spontaneously, the minute ventilation varies based on the patient's breath activity. Consequently, the oxygen concentration varies along with the minute ventilation. This method also requires that the proper flow rate be recalculated each time the ventilator settings are changed. Thus, the true oxygen concentration is never displayed. A further disadvantage is that during exhalation, the continuous flow of oxygen fills the patient circuit. When inspiration occurs, the patient receives 100% oxygen for the first portion of the breath followed by nearly pure air for the remainder of the breath. The result is delivery of wildly varying oxygen concentrations within a single breath.

A second type of gas delivery system uses a mixing box fluidly attached to the ventilator inlet, where a continuous flow of oxygen is injected into the box. The home ventilator draws in mixed air and oxygen from the box for delivery to the patient. This technique eliminates the mixing problem where at first only oxygen, and then only air is delivered to the patient. But this technique is still subject to the problems described above relating to the oxygen variation with minute ventilation, and the repeated recalculation of the flow rate for any change in ventilation.

There is thus a need for a gas delivery system for home ventilation use which does not vary the oxygen concentration with the minute ventilation of the patient. There is a further need for a gas delivery system which does not require continuous recalculation of a gas flow rate. There is a further need for a gas delivery system which delivers a substantially uniform mixture of gases. There is a further need for an ability to visually and accurately display the oxygen concentration over the operating range of the system.

A further difficulty with home ventilator systems is the broad range of operating requirements which are desirable. Current gas blending systems used in hospitals cannot be applied directly to home ventilator use because the devices are designed for use with the pressurized gas sources, over relatively small ranges of operational requirements. A typical blender designed for hospital use has a balance mechanism to substantially balance the pressure of the pressurized gases, and a proportioning mechanism to mix or blend predetermined portions of the gases after their pressures have been substantially balanced.

For example, if the air input pressure was 3500 cmH$_2$O (50 psi), and the oxygen inlet pressure was 2800 cmH$_2$O (40 psi), the pressures of air and oxygen exiting the balance system would typically be 2801 cmH$_2$O and 2800 cmH$_2$O respectively. It is important to note that the balance system does not yield exactly balanced pressures. One such pressure balance mechanism is described in U.S. Pat. No. 3,727,627 to Forrest Bird.

The two nearly balanced gases then enter the proportioning subsystem, the heart of which is typically a double ended poppet operating between an oxygen seat and an air seat. The poppet is positioned between the two seats by a knob/screw actuator to achieve the desired oxygen concentration. As the flow of one gas increases, the flow of the other gas decreases. With the control knob at the 21% position, the poppet is seated on the oxygen seat, allowing only air to flow. At the 100% position, the poppet is seated on the air seat, allowing pure oxygen to flow. Intermediate positions of the poppet yield oxygen concentrations between 21 and 100%.

A typical specification for such a hospital gas blender would be $+/-3\%$ accuracy over a flow range of 12 to 120 liters per minute (lpm), with inlet pressures of about 50 psig. That amounts to a flow ratio of 10:1. The minimum flow through the blender is determined by the permissible pressure drop across the proportioning valve and by the balance capabilities of the balance modules. The pressure drop across the proportioning valve is governed by the follow general equation:

$$\text{Pressure Drop} = K*A*Q^2$$

where: K=constant related to the gas

A=valve area
Q=gas flow rate

Due to the squared relationship, it can be seen that for a 10:1 ratio in the gas flow rate, the corresponding pressure drop would be $(10)^2:1$ or 100:1. As discussed below, these operational capabilities are inadequate for home use.

Home care ventilators typically use one of two available drive systems to actuate a pumping piston which provides the gas pressure to overcome pulmonary resistance and to control the flow rate of the gas into the lungs. The first and simplest drive is a crankshaft type mechanism not unlike that used on a typical automotive engine. The second type of drive uses a direct current (DC) motor coupled to the piston through a ball screw arrangement. The intake flow profiles of these systems vary widely depending on ventilator settings and the drive profile used by the designers of each particular device. Based on selective testing, it is believed that a flow range of 5 to 160 lpm is needed to satisfy the requirements of the various existing ventilators designed for home use.

Since the ventilator must provide the motive force for drawing the blended gases in through the blender, the blender must have a low pressure drop to avoid slowing down the ventilator intake stroke and/or causing excessive energy consumption. It is believed that the pressure drop must not exceed 35 cmH$_2$O through the specified flow range, based on limited empirical testing.

The performance specifications for a home use blender capable of being used with the current spectrum of home ventilators would thus have flow range of 5 to 160 lpm, a maximum pressure drop of 35 cmH$_2$O, a blending range of 21 to 50% of oxygen, and an accuracy of +/−3%. While the air is supplied from the atmosphere at ambient pressure, the oxygen must come from a pressurized source such as a tank or an oxygen concentrator. The pressurized oxygen must be depressurized to ambient pressure using a pressure reducing valve or a throttling orifice feeding a rubber bag. In either case, the pressure of the oxygen can be expected to be 0 to 1 cmH$^2$O above ambient when measured at the proportioning device 12.

To maintain the +/−3% accuracy specification with the 0 to 1 cmH$_2$O oxygen inlet pressure variation from the balance regulator, the minimum pressure drop at 5 lpm must be approximately 5 cmH$_2$O. Using conventional blender technology as previously described, the associated pressure drop at 160 lpm would be $(32)^2*5$, or 5,120 cmH$_2$O.

As can be seen, both the flow and pressure ranges required for the ambient air blender are beyond the capabilities of conventional oxygen blender technology. The ambient pressure blender must be capable of a flow range of 5 to 160 lpm (1:32 ratio), while current blenders have a flow range of 12 to 120 lpm (1:10 ratio). Moreover, the ambient pressure blender must maintain a maximum pressure drop of 35 cmH$_2$O or a maximum pressure ratio of 7:1, while current blenders have a maximum pressure drop of 3500 cmH$_2$O or a maximum pressure ratio of 700:1.

There is thus a need for a home ambient gas blender having greater operational capabilities than previously available. There is a further need for such a system to be small, of simple construction, and reliable, in order to facilitate its use in homes where trained service personnel are not available to continuously monitor the performance of the machine, to adjust it, or to repair it.

SUMMARY OF THE INVENTION

The gas blender of this invention provides a proportioning system which maintains accurate blending of atmospheric air and a pressurized gas such as oxygen over a wide range of flow while maintaining a very small pressure drop.

The blender of this invention advantageously has a poppet and corresponding valve seats configured relative to one another such that a constant ratio of gas flows through each of the two poppet/valve seat combinations as the poppets are moved axially. Structure is provided whereby the adjustment of the oxygen poppet relative to oxygen valve seat by a knob controls the oxygen valve area thus controlling the oxygen flow relative to air.

The oxygen/air blender of this invention advantageously comprises a double poppet means in which movement of two poppets in the same direction simultaneously opens or simultaneously closes two valve seats, in contrast to conventional double poppet arrangements in which movement of the poppets closes one valve seat while opening the other valve seat.

The blender continuously mixes or blends the air and oxygen as they exit the outlet port, thus eliminating the build up of only one gas in the fluid communication lines from the blender to the patient. As the poppet/valve seat design maintains a constant ration of gases, there is thus provided a means of providing a predetermined ratio of mixed gases over a wide range of flow demands. Further, the desired oxygen concentration does not vary through the course of a breath delivery.

The blender of this invention has valve seats designed to cooperate with poppets in such a way that there is a maximum pressure drop of about 35 mm of H$_2$O, thus making this blender usable with a wider variety of home ventilators than previously possible. The low pressure drop advantageously allows the blender to supply the wide flow range demanded by home care ventilators without excessively loading the ventilator intake.

The gas blender of this invention is advantageously used with ventilators used in respiratory and medical uses which blend ambient air with a pressurized gas. A pressure reducer reduces the pressure of a first pressurized gas to substantially ambient pressure. A gas valve seat is placed in fluid communication with the gas from the pressure reducer at substantially ambient pressure. A gas poppet cooperates with the gas valve seat to control the flow of the first gas through the gas valve seat. Similarly, an air valve seat is placed in fluid communication with ambient air, and an air poppet cooperates with the air valve seat to control the flow of air through the air valve seat.

The movement of the air poppet is controlled relative to the movement of the second gas poppet, and the two poppets may be part of a double ended poppet. The air valve seat and the gas valve seat are configured relative to their respective poppets such that movement of the poppets relative to their respective valve seats maintains a constant ratio of air and the second gas flowing through the opening between the valve seats and their respective poppets. Thus, the first and second valve seats are simultaneously opened as the poppets move in a first direction along the poppet axis, and the first and second valve seats are simultaneously closed as the poppets move in the opposite direction along the poppet axis.

There is thus provided first and second valve seat means cooperating with the first and second poppets to control the flow of a different gas through each of the first and second valve seat means, with the valve seat means further cooperating with the first and second poppets to control the flow area through the valve seat means to limit the pressure drop while maintaining a substantially constant ratio of flow for the gases.

Advantageously, a mixing chamber is placed in direct fluid communication with the gas valve seat and the air valve seat to mix the gases passing through those valve seats. More advantageously, one of the valve seats is adjustably postionable relative to its respective poppet to enable the ratio of gases to be selectively determined. This gas ratio will be maintained as the flow of the gases increases and decreases with the demand of the ventilator user. An externally accessible knob connected to the adjustably positionable valve seat to adjustably position the valve seat enables the user to determine the gas ratio by reference to a scale which displays the gas ratio's (e.g., in percentage of oxygen) while simultaneously positioning the adjustable valve seat to achieve the selected ratio.

The ability of gas selector knob to select the oxygen concentration eliminates the need to continuously calculate the minute ventilator variation, and without the need to consult external charts or equations to make the calculations. The ambient pressure air/oxygen blender uses the dual variable orifice system to provide a constant oxygen concentration to the ventilator independent of changes in ventilator minute volume.

In an alternate embodiment of this invention, one of the poppets is configured to be adjustably postionable relative to its respective valve seat to determine the initial ratio of gases flowing through the two valve seats. Similarly, in an alternate embodiment of this invention, one of the poppets is configured to maintain the desired flow ratio. In the preferred embodiment, however, the two poppet diameters (Dp) are fixed, but different, and the diameters of the valve seats (Ds) vary along the axial length of the valve seat according to the equation:

$$Ds = Dp^2 + \frac{4Ke^{cx}\cos(\theta)}{Pi}$$

DESCRIPTION OF THE DRAWINGS

The present invention will be better understood from the description of the preferred embodiment which is given below, taken in conjunction with the drawings in which like reference characters or numbers refer to like parts throughout the description, and in which.

DESCRIPTION OF THE PREFERRED EMBODIMENT

Figure 1:
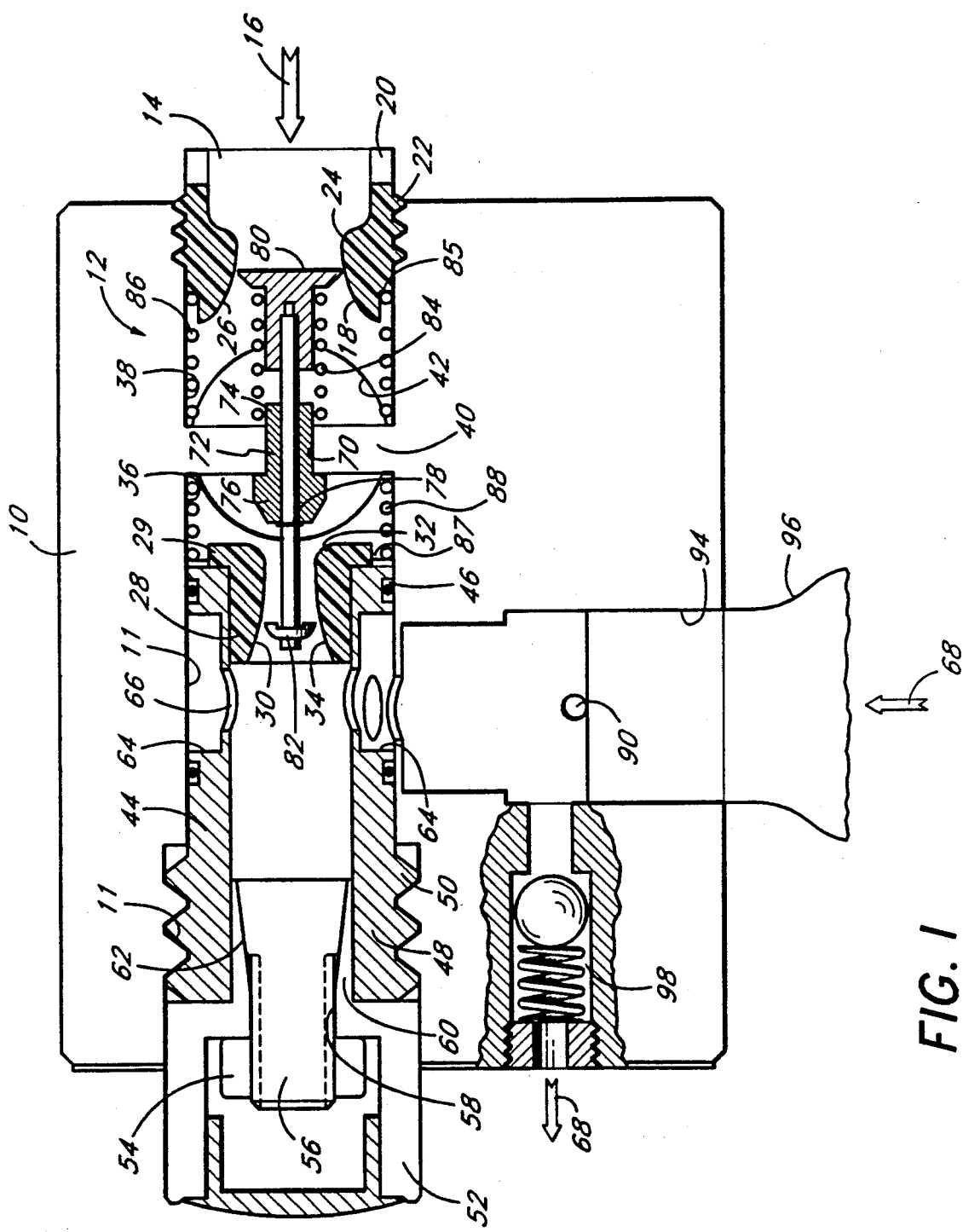
FIG. 1 is a cross-sectional view of the invention.

Referring to FIG. 1, a blender 10 contains a cylindrical cavity 11 into which a gas proportioning device 12 is mounted. The gas proportioning device 12 comprises the structures connected to the cavity 11, including a first gas inlet such as air inlet port 14 which is in fluid communication with a first gas, which in this case is ambient air 16. The air inlet port 14 is in further fluid communication with a first valve seat such as air valve seat 18. The air inlet 14 and valve seat 18 advantageously comprise a first generally tubular segment 20 having external threads 22 on one portion, which threads 22 engage corresponding threads (not shown) in cavity 11 to fasten the tubular segment 20 in the blender housing 10. The segment 20 is connected to the cavity 11 in a gas tight manner so that no gas escapes around the exterior periphery of tubular segment 20.

The valve seat 18 is formed on the inside of the tubular segment 20. The valve seat 18 comprises a first valve seat entry portion referred to as valve seat end 24 and second valve seat end 26, with the ends 24, 26 being generally circular and coaxial, and with second end 26 being generally larger than first end 24. The shape of the valve seat 18 between the first and second ends 24, 26, respectively, is described later.

A second generally tubular segment 28 is aligned coaxially with the tubular segment 20, and located in cavity 11. A second valve seat, such as oxygen valve seat 26, is located on the inside of segment 24. Valve seat 30 has a first end 32, and a second end 34. The ends 32, 34 are generally circular and coaxial, and second end 34 is generally larger than first end 32. The shape of the valve seat 30 between the first and second ends 32, 34, respectively, is described later. Segment 28 has a flange 29 extending radially outward adjacent the first end 32 of segment 28.

The first end 32 of the oxygen valve seat 30 opens into a chamber 36. The second end 26 of the air valve seat 18 opens into a chamber 38. The chambers 36, 38 are defined by the walls of cylindrical cavity 11, the ends of the valve seats 18, 30, and an intervening wall 40. The wall 40 is a radially orientated partition substantially blocking the cavity 11 between the valve seats 18 and 30.

Figure 2:
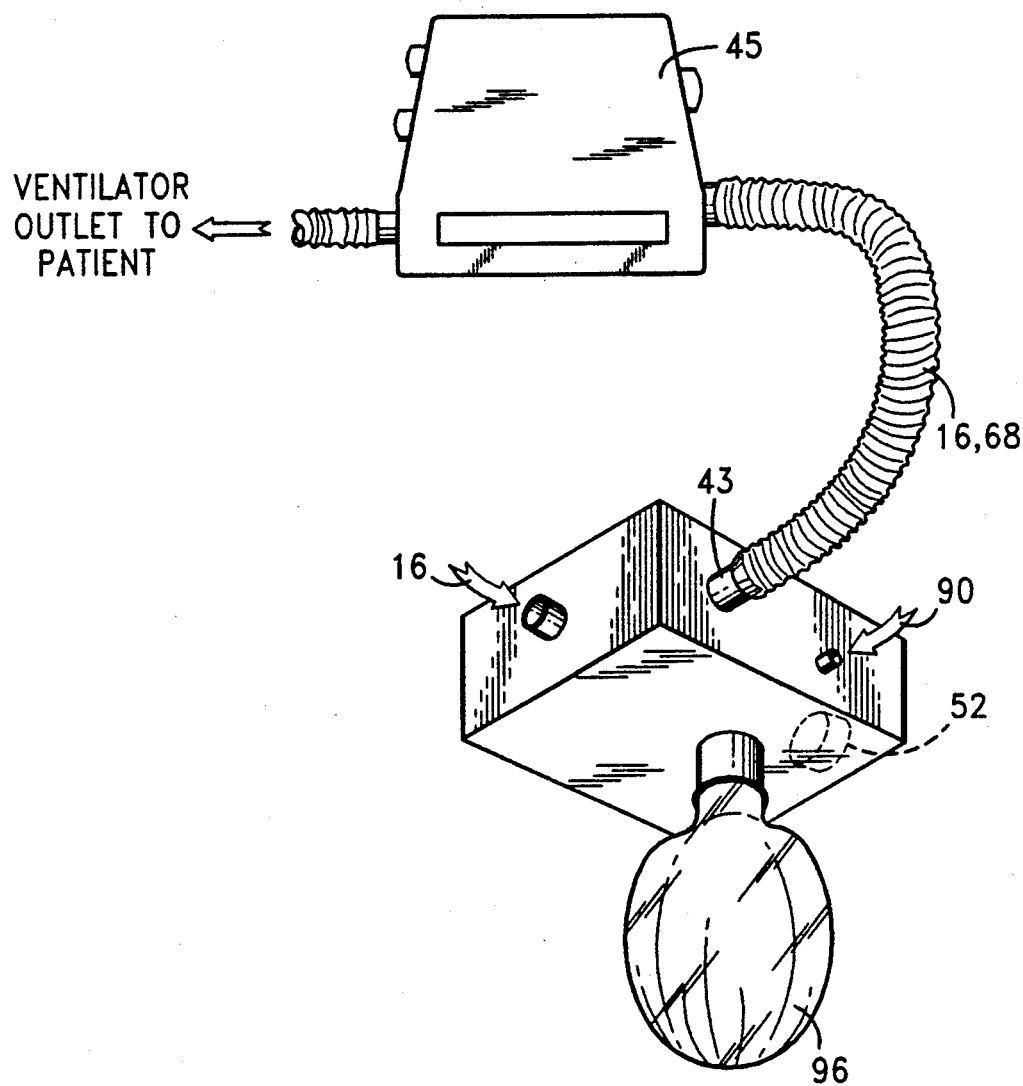
FIG. 2 is a pictorial illustration of the gas blender of this invention connected to a ventilator.

A gas outlet port 42 opens onto both chambers 36, 38 from the side of cavity 11. A tube or other fluid passage means (not shown) is connected to the gas outlet port 42 to provide a fluid communication from the chambers 36, 38 to a user outlet 43 (FIG. 2) which in turn is in fluid communication with a ventilator 45 (FIG. 2).

A third generally tubular segment 44 is located in cavity 11, coaxially aligned with second tubular segment 28. The segment 44 is connected to the cavity 11 in a gas tight manner so that no gas escapes around the exterior periphery of tubular segment 44. A first end 46 of segment 44 overlaps a portion of the segment 28, and abuts the radially outward flange 29 on segment 28 to prevent axial movement of segment 28 relative to tubular section 44 in one axial direction. A second end 48 of segment 44 contains external threads 50 which engage with corresponding threads (not shown) on the inside of cavity 11 to fasten the tube 44 in blender housing 10. The threads 50 are preferably double pitch screw threads.

A knob 52 is connected to the second end 48 of segment 44 by nut 54 which is threadably engaged with one end of a bolt 56 extending through a hole 58 in knob 52. The knob 52 has a tubular cylindrical end 60 having an exterior diameter corresponding to the interior diameter of the inside of generally tubular segment 44. The interior of tubular end 60 is tapered along the axial length of the end 60. The bolt 56 has an end 62 which has an axial taper on its exterior in the opposite direction as the taper in end 60. As the nut 54 tightens the bolt 65, the two oppositely tapered surfaces of the ends 62, 60 wedge the end 60 against the inside of the tubular segment 44 to form a gas tight connection with the segment 44. Rotation of the knob 52 rotates the segment 44, which because of the threads 50, cause the segment 44 to translate as it rotates.

The segment 44 has an annular passage 64 around its periphery. A plurality of apertures or holes 66 extend through the walls of tubular segment 44 to provide fluid communication between the inside of tubular segment 44 and the slot 66. The annular passage 64 is in fluid communication with a source of a second gas, such as oxygen 68. The inside of the tubular segment 44 is in fluid communication with the oxygen valve seat 30 via the second end 34 of valve seat 30.

The wall 40 contains an aperture or hole 70 at its center, along the central axis of segments 20, 28. A tubular sleeve or bushing 72 extends through the hole 70, and has a first end 74 facing the second end 26 of air valve seat 18, and a second end 76 facing the first end 32 of oxygen valve seat 30.

A poppet shaft 78 slidably extends through the hole in bushing 72. A first poppet, such as air poppet 80 is connected to one end of the shaft 78, with a second poppet, such as oxygen poppet 82 connected to the opposite end of shaft 70. The air poppet 80 cooperates with the air valve seat 18 to control the amount of air flowing through the air valve seat 18 into chamber 36. The oxygen poppet 82 cooperates with the oxygen valve seat 30 to control the amount of oxygen flowing through the oxygen valve seat 30 into chamber 38.

Resilient means such as a compression spring 84 extend between the air poppet 80 and the wall 40 to urge the air poppet 80 towards the air valve seat 18 so as to block the flow of air through the air valve seat 18. Advantageously, the coil spring 84 fits over the first end 74 of sleeve 72, and over a portion of poppet 80, so the spring 84 is captivated and prevented from falling into the chamber 38.

Resilient means such as compression spring 86 extend along the interior walls of cavity 11, between the wall 40 and air valve seat 18, to urge the valve seat 18 against the threads 22 holding the valve seat 18 in axial position and thus compensate for thread backlash. Advantageously there is a recessed area 85 around the periphery of the second end 26 of valve seat 18 to captivate the end of the spring 86. Resilient means such as compression spring 88 extend along the interior walls of cavity 11, between the wall 40 and the end of the third segment 44, to urge the tubular segment 44 and the oxygen valve seat 30 against the threads 50 which holds the segment 44 and valve seat 40 in axial position and also compensates for thread backlash. Advantageously, there is an axial space 87 formed between the first end 46 of segment 44, and the radial periphery of flange 29, which captivates the end of spring 88. The springs 84, 86 and 88 provide resilient means for preloading the valve seats and poppets along the axial direction in order to increase the positioning accuracy of these elements.

Oxygen 68 is advantageously supplied either from a pressurized bottle or an oxygen concentrator. The oxygen flow is preferably set by a commonly available flowmeter/valve combination to some level higher than the maximum average ventilator oxygen consumption. This would generally be a low flow in the 1 to 4 lpm range. Alternatively, the oxygen flow could be regulated by a series of fixed orifices at the oxygen inlet. In either event, the pressure of the oxygen gas is reduced by pressure reducing means known in the art before the oxygen reaches the proportioning device 12.

Thus, oxygen 68 at substantially ambient pressure is supplied to the blender 10 through oxygen inlet 90 to the holes 66 in circumferential annular passage 64. A bag attachment port 94 is in fluid communication with the oxygen inlet port 90. The port 94 allows a conventional accumulator bag, partially shown as bag 96, to be attached to port 94 regulate the flow and pressure of the oxygen. As the bag 96 inflates with excess oxygen, the pressure increases. At a predetermined limit pressure, the oxygen vents out past a relief valve 98 which has one end in fluid communication with the accumulator bag 94, and the other end in fluid communication with the atmosphere.

Referring to FIGS. 1 and 2, but primarily to FIG. 1, the operation of the gas blender 10 will be described. Flow through the blender 10 begins when the piston in the ventilator 45 starts the intake stroke. This creates a sub-ambient pressure at the user outlet 43 (FIG. 2) and gas outlet port 42. Ambient air 16 entering through the air inlet port 14 is metered to the desired flow rate by the air poppet 80 and air valve seat 18. In parallel, oxygen 68 at approximately ambient pressure is drawn in from the oxygen inlet port 90, through holes 66, and metered to the desired flow rate by the oxygen poppet 82 and oxygen valve seat 30. The air 16 and oxygen 68 combine as they are drawn out of chambers 36, 38, through gas outlet port 42, to provide the desired oxygen concentration, and the mixed gas flow through the user outlet 43 (FIG. 2) to the ventilator 45.

Oxygen concentration is controlled by moving the tapered oxygen valve seat 30 relative to the oxygen poppet 82, thereby varying the effective valve flow area. The position of the oxygen valve seat 30 is controlled by rotating the oxygen adjustment knob 52 (FIGS. 1 and 2). The circular motion of the knob 30 is converted to linear motion through the use of double pitch screw threads 50. The knob 50 includes an index mark (not shown) which can be positioned relative to the desired oxygen concentration setting on a circular scale (not shown) printed on the blender housing 10. Advantageously, the scale will denote the composition of the gas mixture as a percentage of oxygen. With the oxygen valve 30 and oxygen poppet 82 positioned at a 21% setting, the effective flow area is nearly zero through the oxygen valve seat and poppet. At the 50% position, the oxygen flow area is equal to 0.37 times the air flow area, where the flow area is defined as the area between the respective valve seat and poppet.

The controlling portion of the proportioning device 12 is the poppet-valve seat configuration and arrangement. This proportioning system simultaneously increases the flow areas of both valves in response to high flow demand in order to limit the pressure drop, while maintaining a constant oxygen/air valve area ratio. For example, at a 50% oxygen setting, the initial air valve area is 0.007 sq. in. and the oxygen valve area is 0.0026 sq. in. resulting in an oxygen/air area ratio of 0.37. At 160 lpm, the air and oxygen poppets move together to create flow areas of 0.07 and 0.026 in. sq., respectively, maintaining a constant 0.37 area ratio.

The two poppets 80, 82, are joined together by a common shaft 78 to form a double ended poppet which is biased towards the minimum flow area position by spring 84. The two poppets 80, 82 are different diameters, with the air poppet 80 (0.50 in. diameter) having a larger diameter than oxygen poppet 82 (0.25 in. diameter). When a subambient pressure exists at the blender outlet port 42, the pressure differential across the two poppets 80, 82 is equal, but the net forces are unequal due to the difference lo in poppet diameters. For a given pressure, a larger force will be exerted on the larger air poppet 80 because of its larger surface area with respect to the smaller oxygen poppet 82. This force imbalance causes the poppets 80, 82 to move away from the valve seats 18, 30, thus creating a larger flow area in response to the flow demand. There is thus provided a double ended poppet means of differing poppet diameters for varying the flow area through the valve seats 80, 82 in response to varying flow demand.

When the patient is exhaling, no mixture of oxygen and air is provided to the patient, or to the ventilator 45 (FIG. 2) through port 42. Because the oxygen provided to the blender 10 is at a constant pressure, any excess oxygen flow is stored in flexible accumulator bag 96 attached to the bag port 94. When the bag 96 is fully inflated, the excess oxygen is bypassed to the atmosphere through relief valve 98. Advantageously, the relief valve 98 cooperates wit the bag 96 to maintain the pressure in the bag 96 at about 1 cmH$_2$O. During the ventilator intake phase, high oxygen flows can be drawn from the accumulator bag 96.

As previously indicated, the poppet/seat configuration is specially configured to simultaneously increase the flow areas of both valves in response to high flow demand in order to limit the pressure drop, while maintaining a constant oxygen/air valve area ratio. In order to accomplish this, an axial change in position of either poppet 80, 82 must increase or decrease the flow area linearly proportional to the areas immediately preceding the change in position. For example, if the air valve flow area between air poppet 80 and air valve seat 18 increases by 10%, the oxygen valve flow area between the oxygen valve 82 and the oxygen valve seat 30 must also increase 10%, regardless of the valve area at the time of the change.

Mathematically, this can be stated as follows; the first derivative of the valve area function (dA/dx) must be linearly proportional to the area at any x poppet position. By definition, the only mathematical expression that is linearly proportional to its own first derivative is the exponential function (e). Therefore, the flow area must fulfill equation 1, $$A = k e^{cx} \qquad (1)$$

where C and k are constants which represent the gain and initial area of the profiles of valve seats 18, 30.

The shape of the flow area between the poppets 80, 82, and their respective valve seats 18, 30, is believed to be a frustrum. The formula for the area of the frustrum is given in Equation 2.

$$A = (Pi/s)S(Dp + Ds) \qquad (2)$$

Where:
Dp = Poppet Diameter
Ds = Seat Diameter
$S = (Ds - Dp)/(2\cos\theta)$
Combining Equations 1 and 2 yields:

$$Ds = Dp^2 + \frac{4Ke^{cx}\cos(\theta)}{Pi} \qquad (3)$$

Since both Ds and theta are unknown at this point, a numerical solution must be used to solve for the desired seat profile. Two points X1 and X2 were selected along the axial travel path of poppets 80, 82. As X2 − X1 approaches zero, the shape of the adjacent portion of the valve seats 80, 82 can be assumed to be a straight line. Using this assumption and simple trigonometry an independent expression relating Ds1 and DS2 was developed as follows:

$$D_{s1} + 2(X2 - X1)\sin\theta\cos\theta = Ds2 \qquad (4)$$

Letting (X2 − X1) = I and substituting (3) for Ds1 and Ds2 in equation 4 yields:

$$\left[ D_p^2 + \frac{4Ke^{cx1}\cos\theta}{\pi} \right]^{\frac{1}{2}} + 2I\sin\theta\cos\theta = \left[ D_p^2 + \frac{4Ke^{c(I+x1)}\cos\theta}{\pi} \right]^{\frac{1}{2}} \qquad (5)$$

Through numerical iteration using Equation 5, the value of theta for every poppet position X1 can be determined. Substituting this known value of theta into Equation 3 yields the diameter of valve seats 18, 30, for each X position. The profile of valve seats 18, 30 can then be developed by plotting Ds1 vs X.

Using the above equations and numerical analysis techniques a detailed solution for both the air and oxygen seat profiles can be obtained.

As may be seen from FIG. 1, the air valve seat 18 has a contoured shape in which the first end 24 is generally smaller than the second end 26, such that the wider end opens into the chamber 36. The oxygen valve seat 30 has a contoured shape in which the first end 32 is smaller than the second end 34, with the smaller end 32 opening into the chamber 38. Both of the valve seats 18, 30 are orientated with their larger ends 28, 34 opening in the same direction. There is thus advantageously supplied a double poppet means in which movement of poppets 80, 82 in the same direction simultaneously open or simultaneously close both valve seats 18, 30, in contrast to conventional double poppet arrangements in which movement of the poppets closes one valve seat while opening the other valve seat.

While the blender 10 has been described as having the valve seats 18, 30 configured to provide the desired flow ratio, it is believed possible to have the poppets 80, 82 specially configured and to have the valve seats 18, 30 of normal construction. In a similar vein, it is believed possible to have both the poppets 80, 82, and valve seats 18, 30 configured to define the desired flow area between the poppets and their respective valve seats as the poppets the poppets and their respective valve seats as the poppets move axially. While the oxygen valve seat 30 is shown as being adjustably positioned to vary the ratio of the gases, it is also believed possible to vary the position of the air valve seat 18, or to have one of the poppets 80, 82 threadably engage the shaft 78 so that one or both of the poppets 80, 82 could be adjustably positioned to vary the ratio of the gasses.

While the valve seats 18, 30 have been shown in one particular orientation or arrangement, it is believed possible to vary the orientation of the valve seats and the respective poppets while still achieving the ability to maintain constant ratio's of flow through the valve seats, although such change in orientation or arrangement may require additional linkages to maintain correct relative movement of the poppets and valve seats, or require additional fluid communication passages to correctly orientate the flow of gases through the valves seats.

The blender 10 of this invention advantageously has the poppet and corresponding valve seats configured relative to one another such that a constant ratio of gas flows through each of the two poppet/valve seat combinations as the poppets 80, 82 are moved axially. The adjustment of oxygen poppet 82 relative to oxygen valve seat 30 by knob 52 allows the ratio of air and oxygen to be preset, and once preset, the poppet/valve seat design maintains that ratio.

The blender 10 mixes or blends the air and oxygen as they exit the outlet port 42, thus eliminating the build up of only one gas in the fluid communication lines from the blender 10 to the patient. As the poppet/valve seat design maintains a constant ratio of gases, there is thus provided a means of providing a predetermined ratio of mixed gases over a wide range of flow demands. Further, the desired oxygen concentration does not vary through the course of a breath delivery.

The ability of gas selector knob 52 to select the oxygen concentration eliminates the need to continuously calculate the minute ventilator variation, and without the need to consult external charts or equations to make the calculations. The ambient pressure air/oxygen blender uses the dual variable orifice system to provide a constant oxygen concentration to the ventilator 45 (FIG. 2) independent of changes in ventilator minute volume.

The blender 10 of this invention has valve seats 18, 30 designed to cooperate with poppets 80, 82 in such a way that there is a maximum pressure drop of 35 mm of H₂O across the proportioning device 12, thus making this blender 10 usable with a wider variety of home ventilators than previously possible. The low pressure drop advantageously allows the blender 10 to supply the wide flow range demanded by home care ventilators without excessively loading the ventilator intake.

Although an exemplary embodiment of the invention has been disclosed for purposes of illustration, it will be understood that various changes, modifications and substitutions may be incorporated in such embodiment without departing from the spirit of the invention as defined by the claims which follow.

I claim:

1. A ventilator apparatus for use in respiratory and medical applications comprising a gas blender for blending ambient air with a gas from a pressurized source which has been reduced to substantially ambient pressure, said gas blender further comprising
    a first valve seat in fluid communication with a first gas at substantially ambient pressure;
    a second valve seat in fluid communication with a second gas at substantially ambient pressure;
    a double ended poppet having a first poppet cooperating with the first valve seat to control the flow of the first gas through the first valve seat, and having a second poppet cooperating with the second valve seat to control the flow of the second gas through the second valve seat, the first and second valve seats being configured relative to their respective poppets such that movement of the poppets relative to their respective valve seats maintains a constant ratio of the first and second gases flowing through the opening between the valve seats and their respective poppets.

2. An apparatus as defined in claim 1, wherein one of said first or second valve seats further comprise adjustment means for positioning a respective one of said poppets to vary the ratio for the first and second gases flowing between the valve seats and their respective poppets.

3. An apparatus as defined in claim 1, wherein one of said poppets further comprises adjustment means for positioning itself relative to its respective valve seat.

4. An apparatus as defined in claim 1, wherein diameters of said poppets are constant, and the valve seats are configured according to the equation $$Ds = Dp^2 + \frac{4Ke^{cx}\cos(\theta)}{Pi}.$$

5. An apparatus as defined in claim 1, wherein diameters of said poppets are unequal, said poppets cooperating with the first and second valve seats to define a flow area for a respective gas through each of the first and second valve seats in response to a variation in flow demand for the gases.

6. An apparatus as defined in claim 5, wherein the first and second poppets and the first and second valve seats define flow areas through the valve seats according to the following relationship:

$$A = ke^{cx}.$$

7. A ventilator apparatus for use in respiratory and medical applications comprising a gas blender for blending a first and second gas at substantially ambient pressure, said gas blender further comprising
    a first valve seat in fluid communication with a first gas at a first pressure;
    a second valve seat in fluid communication with a second gas at substantially the first pressure;
    a double ended poppet having a first poppet cooperating with the first valve seat to control the flow of the first gas through the first valve seat, and having a second poppet cooperating with the second valve seat to control the flow of the second gas through the second valve seat, the first and second poppets being of different diameters, the first and second valve seats being configured relative to their respective poppets such that movement of the poppets relative to their respective valve seats maintains a constant ratio of the first and second gases flowing through the opening between the valve seats and their respective poppets.

8. An apparatus as defined in claim 7, wherein the first and second poppets and the first and second valve seats define flow areas through the valve seats according to the following relationship:

$$A = ke^{cx}.$$

9. A ventilator apparatus for use in respiratory and medical applications comprising a gas blender for blending a first and a second gas at substantially ambient pressure, said gas blender further comprising
    a first valve seat in fluid communication with a first gas at a first pressure;
    a second valve seat in fluid communication with a second gas at substantially the first pressure;
    a double ended poppet having a first poppet cooperating with the first valve seat to control the flow of the first gas through the first valve seat, and having a second poppet cooperating with the second valve seat to control the flow of the second gas through the second valve seat, the first and second poppets being of different diameters, one of the valve seats having adjustment means for adjusting the amount of gas passing through the valve seat relative to a predetermined poppet position.

10. A ventilator apparatus for use in respiratory and medical applications comprising a gas blender for blending a first and a second gas at substantially ambient pressure, said gas blender further comprising
a first valve seat in fluid communication with a first gas at a first pressure;
a second valve seat in fluid communication with a second gas at substantially the first pressure;
a double ended poppet having a first poppet cooperating with the first valve seat to control the flow of the first gas through the first valve seat, and having a second poppet cooperating with the second valve seat to control the flow of the second gas through the second valve seat, the first and second poppets being of different diameters, with the shape of the valve seats being determined according to the equation:

$$Ds = Dp^2 + \frac{4Ke^{cx}\cos(\theta)}{Pi}.$$

11. A ventilator apparatus for sue in respiratory and medical applications comprising a gas blender for blending a first and a second gas at substantially ambient pressure, said gas blender further comprising
a first valve seat in fluid communication with a first gas at a first pressure;
a second valve seat in fluid communication with a second gas at substantially the first pressure;
a double ended poppet having a longitudinal axis, said double ended poppet being movable along the axis and having;
a first poppet cooperating with the first valve seat to control the flow of the first gas through the first valve seat, and having a second poppet cooperating with the second valve seat to control the flow of the second gas through the second valve seat, the first and second valve seats being simultaneously opened as the poppets move in a first direction along the axis, the first and second valve seats being simultaneously closed as the poppets move in the opposite direction along the axis.

12. An apparatus as defined in claim 11, wherein the valve seats are configured to maintain a constant ratio of gases as the poppets move axially.

13. An apparatus as defined in claim 12, wherein on of the valve seats further comprises adjustment means for varying the ratio of the first and second gases flowing between the valve seats and the respective poppets.

14. A ventilator apparatus for use in respiratory and medical applications comprising a gas blender for blending a first and a second gas at substantially ambient pressure, said gas blender further comprising
double ended poppet means for varying gas flow said poppet means further comprising a first and second ends of different diameters cooperating with first and second valve seat means for controlling the flow of a different gas through each of the first and second valve seat means.

15. An apparatus as defined in claim 14, wherein the double ended poppet means and the first and second valve seat means define flow areas through the valve seats according to the following relationship:

$$A = ke^{cx}.$$

16. An apparatus as defined in claim 15, wherein the double ended poppet means is resiliently urged toward a configuration allowing minimum flow through the valve seats means.

17. An apparatus as defined in claim 15, further comprising gas blend ratio adjustment means for adjustably setting the valve seat means relative to the poppet means and determining initial flow area between the valve seat means and the poppet means.

18. An apparatus as defined in claim 15, wherein the double ended poppet means comprises first and second poppets having different diameters determined according to the following equation, and wherein the first and second valve seat means comprise first and second valve seats configured according to the following equation:

$$Ds = Dp^2 + \frac{4Ke^{cx}\cos(\theta)}{Pi}.$$

19. A method of blending ambient air with a pressurized gas in a ventilator apparatus for respiratory and medical uses, comprising the steps of:
reducing the pressure of a first pressurized gas to substantially ambient pressure;
varying the flow area between a gas valve seat in fluid communication with the reduced pressure gas and between a gas poppet to control the flow of the first gas through the gas valve seat;
placing an air valve seat in fluid communication with ambient air;
placing an air poppet in cooperative engagement with the air valve seat to control the flow of air through the air valve seat;
coordinating the movement of the air poppet with the movement of the gas poppet to simultaneously vary the flow of the two gases to maintain a constant ratio of the flow of air and the second gas.

20. A method as defined in claim 19, comprising the further step of:
placing the two gases in direct fluid communication with a mixing chamber to mix the gases passing through the two valve seats.

21. A method as defined in claim 20, wherein the movement of the two poppets are mechanically and directly coordinated.

22. A method as defined in claim 19, comprising the further step of adjustably positioning one of the valve seats relative to its respective poppet to determine an initial ratio of gases flowing through the two valve seats.

23. A method as defined in claim 19, comprising the further step of adjustably positioning one of the poppets relative to its respective valve seat to determine an initial ratio of gases flowing through the two valve seats.

24. A method as defined in claim 19, wherein the coordinating step comprises coordinating the movement of the poppets such that the poppets move in the same direction.

25. A method of blending two gases of substantially ambient pressure for use in a ventilator used in respiratory and medical applications, comprising the steps of:
placing a first valve seat and a first end of a double ended poppet in fluid communication with a first gas at substantially ambient pressure to define a first flow area for the first gas through the first valve seat;

placing a second valve seat and a second end of a double ended poppet in fluid communication with a second gas at substantially ambient pressure to define a second flow area for the second gas through the second valve seat;

configuring the first and second valve seats relative to their respective poppets such that movement of the poppets relative to their respective valve seats maintains a constant ratio of the first and second gases flowing through the first and second flow areas.

26. A method of blending gases as defined in claim 25 comprising the further step of:

adjustably positioning one of the valve seats relative to its respective poppet to vary the ratio of the first and second gases flowing through the positioned valve seat and its respective poppet.

27. A method of blending gases as defined in claim 25, comprising the further steps of:

configuring the diameters of the poppets to be of two different circular diameters; and configuring the valve seats according to the equation $$Ds = Dp^2 + \frac{4Ke^{cx}\cos(\theta)}{Pi}.$$

28. A method of blending gases as defined in claim 27 comprising the further step of configuring the first and second poppets and the first and second valve seats to define first and second flow areas according to the following relationship:

$$A = ke^{cx}.$$

29. A method of blending ambient air with a gas from a pressurized source which as been reduced to substantially ambient pressure for use in a ventilator apparatus used in respiratory and medical applications, comprising the steps of:

placing a first valve seat in fluid communication with a first gas at substantially ambient pressure;

placing a second valve seat in fluid communication with ambient air;

configuring a poppet into a double ended poppet having a first and a second end, and positioning that poppet so the first poppet end cooperates with the first valve seat to control the flow of the first gas through the first valve seat, and further positioning the poppet so the second poppet end cooperates with the second valve seat to control the flow of the second gas through the second valve seat, the first and second poppets being configured to be of different diameters;

providing user adjustment of the amount of one of the gases passing through its valve seat by positioning one of the valve seats relative to its poppet.

30. A method of blending two gases of substantially ambient pressure for a ventilator used in respiratory and medical uses, comprising the steps of:

placing a first valve seat in fluid communication with a first gas at a first pressure;

placing a second valve seat in fluid communication with a second gas at substantially the first pressure;

controlling the flow of the first gas through the first valve seat by use of a first end of a double ended poppet which cooperates with the first valve seat;

controlling the flow of the second gas through the second valve seat by use of a second end of the double ended poppet which cooperates with the second valve seat;

configuring the first and second poppets to be of different diameters; and configuring the shape of the valve seats according to the equation:

$$Ds = Dp^2 + \frac{4Ke^{cx}\cos(\theta)}{Pi}.$$

31. A method of blending two gases of substantially ambient pressure for a ventilator used in respiratory and medical uses, comprising the steps of:

placing a first valve seat in fluid communication with a first gas at a first pressure;

placing a second valve seat in fluid communication with a second gas at a second pressure;

positioning and moving a first poppet along an axis so the first poppet cooperates with the first valve seat to control the flow of the first gas through the first valve seat;

positioning and moving a second poppet along the same axis so the second poppet cooperates with the second valve seat to control the flow of the first gas through the second valve seat;

simultaneously opening the first and second valve seats by moving the poppets in a first direction along the axis, and simultaneously closing the first and second valve seats being as the poppets move in the opposite direction along the axis.

32. A method of blending gases as defined in claim 31, comprising the further step of configuring the valve seats so they maintain a constant ratio of gases as the poppets move axially.

33. A method of blending gases as defined in claim 32, comprising the further step of:

adjustably positioning one of the valve seats relative to its respective poppet to vary the ratio of the first and second gases flowing between the valve seats and their respective poppets.

34. A method of blending two gases at substantially ambient pressure for a ventilator used in respiratory and medical uses, comprising the steps of:

positioning a first poppet relative to a first valve seat, and a second poppet relative to a second valve seat to control the flow of a different gas through each of the first and second valve seats;

simultaneously controlling the flow through both of the valve seats to limit the pressure drop while maintaining a substantially constant ratio of flow for the two gases.

35. A method of blending gases as defined in claim 34, comprising the further step of:

configuring the first and second poppets and valve have constant, but different diameters determined according to the following equation, and configuring the first and second valve seats according to the following equation:

$$Ds = Dp^2 + \frac{4Ke^{cx}\cos(\theta)}{Pi}.$$

36. A method of blending two gases at substantially the same pressure for a ventilator used in respiratory and medical uses, comprising the steps of:
   placing a first gas in fluid communicating with a first valve seat;
   placing a second gas in fluid communicating with a second valve seat, the first and second gases being at substantially the same pressure; and
   using a double ended poppet having first and second ends of different diameters in cooperation with the first and second valve seats to simultaneously control the flow seats in response to a variation in flow demand for the gases.

37. A method of blending gases as defined in claim 36, comprising the further step of:
   configuring the poppet and the first and second valve seats to define flow areas through the valve seats according to the following relationship:

$$A = ke^{cx}.$$

38. A method of blending gases as defined in claim 36, comprising the further step of:
   resiliently urging the double ended poppet toward a configuration allowing a predetermined minimum flow through the two valve seats.

39. A method of blending gases as defined in claim 37, comprising the further step of adjustably setting the initial flow area between the valve seats and the respective poppet ends by positioning one of the valve seats relative to its poppet end.

40. A method of blending gases as defined in claim 37, comprising the further step of configuring the two ends of the poppet to have different diameters determined according to the following equation, and configuring the first and second valve seats according to the following equation:

$$Ds = Dp^2 + \frac{4Ke^{cx}\cos(\theta)}{Pi}.$$

* * * * *